United States Patent
Kötitz et al.

(10) Patent No.: US 6,979,574 B1
(45) Date of Patent: Dec. 27, 2005

(54) PROCESS FOR DETECTING BINDING REACTIONS WITH USE OF THE MEASUREMENT OF THE RELAXATION OF THE DOUBLE REFRACTION OF MAGNETIC PARTICLES

(75) Inventors: Roman Kötitz, Jena (DE); Julia Lange, Berlin (DE); Julian Browaeys, Paris (FR); Régine Perzynski, Paris (FR); Jean-Claude Bacri, Paris (FR); Virginie Ponsinet, Sucy-en-Brie (FR); Thomas Rheinländer, Lörrach (DE)

(73) Assignee: Institut fuer Diagnostik Forshung GmbH, Berlin (DE)

( * ) Notice: Subject to any disclaimer, the term of this patent is extended or adjusted under 35 U.S.C. 154(b) by 753 days.

(21) Appl. No.: 09/631,630

(22) Filed: Aug. 4, 2000

Related U.S. Application Data
(60) Provisional application No. 60/148,686, filed on Aug. 16, 1999.

(30) Foreign Application Priority Data

Aug. 6, 1999 (DE) .......................................... 199 38 384

(51) Int. Cl.⁷ ............................................. G01N 33/553

(52) U.S. Cl. ..................... 436/526; 436/525; 436/501; 436/518; 436/524; 436/149; 436/64; 436/65; 436/173; 436/806; 435/4; 435/7.1; 435/7.2; 435/7.21; 435/7.22; 435/7.23; 435/7.4

(58) Field of Search ................................ 436/526, 525, 436/501, 524, 518, 149, 65, 173, 64, 806; 435/7.1, 4, 7.2, 7.21, 7.22, 7.23, 7.4

(56) References Cited

U.S. PATENT DOCUMENTS 6,027,946 A * 2/2000 Weitschies et al.
6,485,985 B1 * 11/2002 Weitschies et al.

FOREIGN PATENT DOCUMENTS

DE          195 03 644        8/1996

OTHER PUBLICATIONS

Koetitz et al., "Determination of the binding reaction between avidin and biotin by relaxation measurements if magnetic nanoparticles", *Journal of Magnetism and Magnetic Materials*, Apr. 1999, pp. 62–68, vol. 194, No. 1–3.
Weitschies et al., "Determination of relaxing or remanent nanoparticle magnetization provides a novel binding–specific technique for the evaluation of immunoassays." *Pharmaceutical and Pharmacological Letters*, 1997, pp. 5–8, vol. 7, No. 1.
Barci et al., "Magnetic transient birefringence of ferrofluids: particle size determination", *Journal De Physique*, Aug. 1987, pp. 1385–1391, vol. 48, No. 8.
Barci et al., "Ferrofluid viscometer", *Journal De Physique Lettres*, Dec. 15, 1985, pp. L1199–L1205, vol. 46, No. 24.
Hasmonay et al., "Optical properties if nickel ferrite ferrofluids", *Journal of Magnetism and Magnetic Materials*, Jul. 1999, pp. 195–199, vol. 201, No. 1–3.

* cited by examiner

*Primary Examiner*—Christopher L. Chin
*Assistant Examiner*—Pensee T. Do
(74) *Attorney, Agent, or Firm*—Millen, White, Zelano & Branigan, P.C.

(57) ABSTRACT

The invention relates to a new process for detecting analytes or binding reactions using measurement of the double refraction, as well as the use of the compounds in analytical chemistry that are necessary for this purpose.

41 Claims, 4 Drawing Sheets

DIAGRAMMATIC VIEW OF THE EXPERIMENTAL SET-UP

Figure 1:
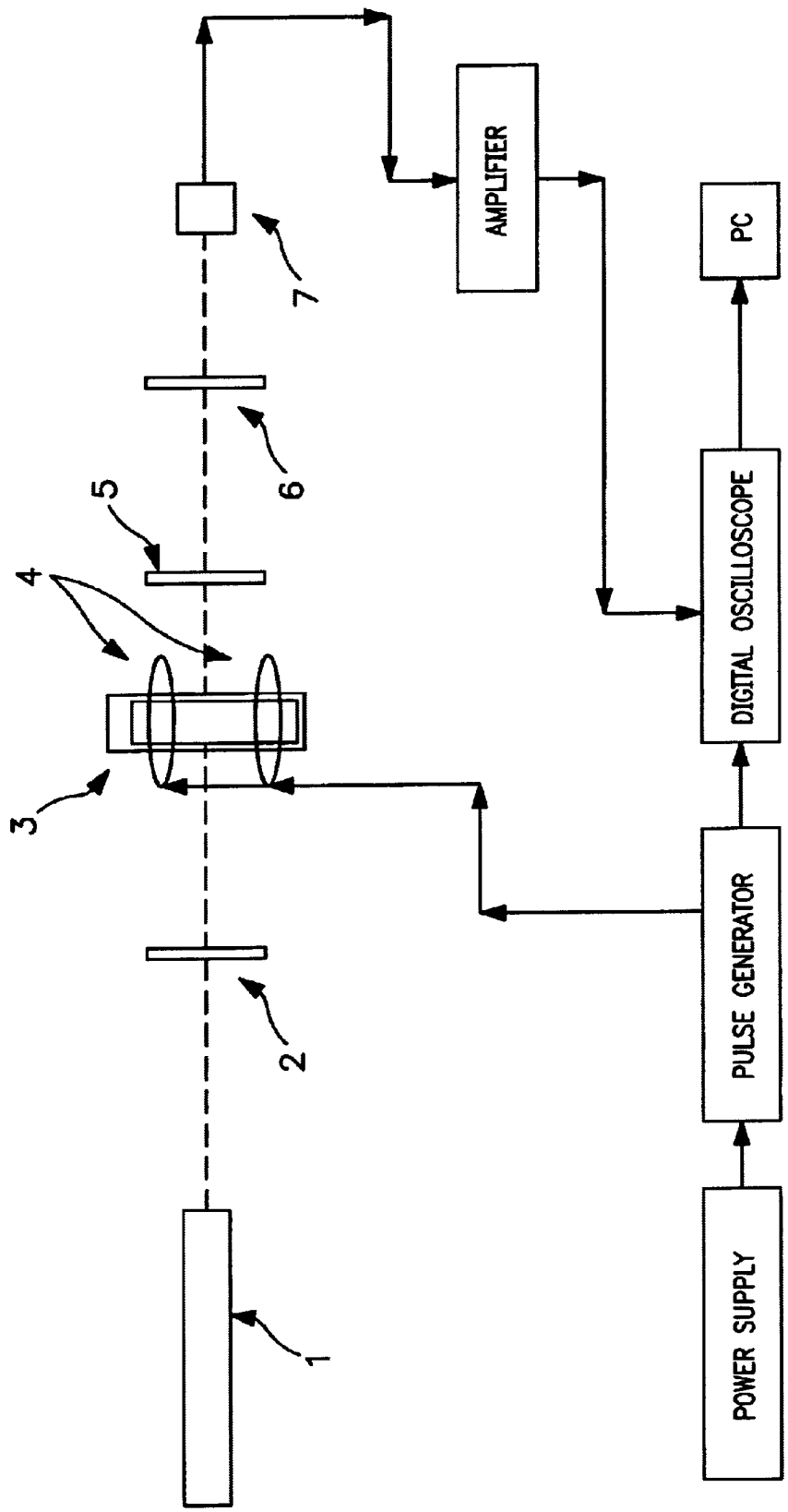

PROCESS FOR DETECTING BINDING REACTIONS WITH USE OF THE MEASUREMENT OF THE RELAXATION OF THE DOUBLE REFRACTION OF MAGNETIC PARTICLES

This application claims the benefit of the filing date of U.S. Provisional Application Ser. No. 60/148,686 filed Aug. 16, 1999.

The invention relates to a new in-vitro process for detection of analytes or binding reactions, in which ferromagnetic or ferrimagnetic substances are used as labeling in immunoassays or other binding assays, which is characterized in that the relaxation of the double refraction is intended as a measurement variable, as well as the use of suitable ferromagnetic or ferrimagnetic substances in this process.

German Patent DE 195 03 664 C2 describes a process for magnetorelaxometric quantitative detection of analytes in liquid and solid phases. In this case, this is an assay process, in which first structure-specific substances with freely movable ferrimagnetic or ferromagnetic colloidal particles of suitable magnetic relaxation time and with suitable magnetic moment are labeled, and then these labeled structure-specific substances are used in a liquid or immobilized sample that is to be measured. The sample that is to be measured is then magnetized with a magnetic field that is applied from the outside and, after the external field is turned off, the relaxation of the magnetization of the colloidal particles is measured with the use of suitable magnetic field sensors, whereby the relaxation time that is changed by specific binding and/or the relaxation amplitude that is changed by the extent of the binding is used for analysis. In this way, it is possible, e.g., to determine quantitatively the concentration of an antibody vis a vis collagen.

The drawback of the invention consists in that, i.a., the experimental set-up for implementing the process is very expensive. To measure the magnetic field, SQUIDs (Superconducting Quantum Interference Devices) are used that are located in a special cryostat and must be cooled in an expensive manner with liquid helium. In addition, magnetic noise fields must be suppressed for highly sensitive measurements, and thus at this time, the process can be carried out only in a very a expensive magnetically shielded space. Further problems of magnetic measuring techniques are produced by a technically produced dead time, by which data on the decisive initial part of the relaxation signal are not available, as well as a background signal, which must be compensated.

It is also known that ferrofluids show double refraction, if when a magnetizing field is applied, the ferrimagnetic or ferromagnetic colloidal particles of the ferrofluid line up overall in the direction of the field. After the field is turned off, a relaxation of the double refraction then results by thermal reorientation of the magnetic particles. This relaxation signal is also known as a "magnetic transient birefringence." The time constant of this relaxation process depends on the temperature, the viscosity of the carrier liquid and the hydrodynamic volume of the magnetic particles. By measuring the relaxation of the double refraction, the hydrodynamic volume of the magnetic particles can then be determined (see Bacri et al., "Magnetic Transient Birefringence of Ferrofluids: Particle Size Determination," J. Physique 48 (1987), 1385–1391).

The object of this invention is to develop a new in-vitro process for detecting analytes or binding reactions with use of magnetic particles, which overcomes the drawbacks of the known process according to DE 195 03 664 C2, is especially significantly simpler to perform, and makes it possible to detect the analytes or binding reactions with a comparable sensitivity.

This object is achieved by this invention, which is defined in the claims.

It has been found that the detection of analytes or binding reactions is possible in liquid phases if ferromagnetic or ferrimagnetic substances are used as labeling in immunoassays or other binding assays, and the relaxation of the double refraction is determined as a measurement variable. The new process no longer detects the magnetic field of the sample that dies down by the reorientation of the magnetic moments of the ferromagnetic or ferrimagnetic substances, but rather the relaxation of the double refraction as a measure of the reorientation of the ferromagnetic or ferrimagnetic substances in the sample. It has been found, surprisingly enough, that the sensitivity of the measurement of the relaxation of the double refraction is comparable to the sensitivity of the direct measurement of the relaxation of the magnetization of the sample.

The new process is based on a special measuring technique, which makes it possible to produce a double refraction according to the orientation of the ferromagnetic or ferrimagnetic substances by application of an external magnetic field in the sample and to determine the relaxation of the double refraction after the external magnetic field is turned off. The drawbacks of the known measuring technique that are described above are overcome with the new process.

The process is implemented with a measurement arrangement that first allows an orientation of the ferromagnetic or ferrimagnetic substances of the sample that is to be examined with use of a suitable magnetic field and then makes possible the measurement of the relaxation of the double refraction of these substances.

This measurement arrangement generally contains a device for producing polarized light, a device for receiving the sample, a device for magnetizing the sample with magnetic pulses or a magnetic field of variable frequency, as well as a device for analysis of the polarization direction of polarized light.

An embodiment of a device that is suitable for implementing the process comprises, e.g., an optical bank, on which a laser, a polarizer, an optical cell with the sample, an analyzer and a detector are arranged. The sample is introduced into a magnetizing coil, which is actuated by a power supply and a pulse generator, and the measurement signal is fed to a computer for evaluation. Such a device is depicted diagrammatically in FIG. 1. In this case, (1) shows an He-Ne-laser, (2) a polarizer, (3) an optical cell with a sample, (4) the magnetizing coils, (5) a λ/4-plate (optional), (6) an analyzer and (7) a photodetector. Such a device is described in, e.g., J. Physique Lett., Vol. 46, 1985, L-1199–L-1205.

After the sample is magnetized (strength of the pulses, e.g., 10 mT; period, e.g., 2 ms; pause, e.g. 20 ms) and after the field is turned off, the relaxation of the double refraction can be measured in an especially sensitive manner using highly sensitive photosensors, such as, e.g., pin-diodes or avalanche diodes. To improve the signal-noise ratio, several measurements are averaged.

As an alternative to measuring the relaxation of the double refraction in the time range, a measurement of the double refraction in the frequency range can also be performed. In this case, a number of measurements are made, in which the sample is exposed to alternating magnetic fields, and the double refraction is detected with distance and phase relative to the magnetizing field. This measurement variable can be transformed into a complex form, whereby data on the relaxation times of the double refraction can be obtained from real and imaginary parts of this complex double refraction.

As was already described in German Patent DE 195 03 664 C2, after an external magnetizing field is turned off, the magnetization of freely moveable ferromagnetic or ferrimagnetic colloidal particles relaxes within the measuring time by two different mechanisms:

(i) Turning of the whole colloidal particle inside the surrounding liquid, whereby the time constant depends on the hydrodynamic diameter of the particles, the viscosity of the carrier liquid, and temperature, which mainly reflects parameters of the environs of the particles; this mechanism is also referred to below as Brownian relaxation and ii) Turning of the internal magnetizing vector inside the magnetic core of the colloidal particles, whereby the time constant depends in a very sensitive manner on material and shape (the anisotropy constants of the particle material used), volume and the temperature of the magnetic core of the particles that are used. These are basically intrinsic parameters of the particles; this mechanism is also referred to below as Neelian relaxation.

These two mechanisms also determine the change in magnetization of a system of freely moveable ferromagnetic or ferrimagnetic colloidal particles when an external magnetic field is activated.

In the absence of an external magnetic field, ferrofluids do not show any double refraction. A requirement for the production of the double refraction is the turning of the whole particle through an external magnetic field, in other words, a reaction to the applied magnetic field according to the Brownian mechanism. Particles that react to an external magnetic field according to the Neelian mechanism do not contribute to the double refraction. The process with shorter relaxation time is predominant. Only particles whose Brownian relaxation time is shorter than their Neelian relaxation time therefore contribute to the double refraction.

If ferromagnetic or ferrimagnetic substances are used in immunoassays or other binding assays, their Brownian relaxation under the measuring conditions in the unbonded state proceeds faster than the Neelian relaxation, and the proportion of unbonded magnetic markers in addition to unbonded magnetic markers that are present simultaneously in the measuring sample can be determined by the change in the predominant relaxation mechanism or by the scaling-up of the particle volume.

As in the process that is described in DE 195 03 664 C2, the structure-specific substances that bind the analytes are first labeled with ferrimagnetic or ferromagnetic colloidal particles. These magnetically labeled structure-specific substances are added to the liquid or immobilized sample that is to be measured, and the sample that is to be measured is magnetized with a magnetic field that is applied from the outside. After the external field is turned off, the relaxation of the double refraction or the double refraction in the frequency range is determined.

The process is preferably implemented so that
(i) the structure-specific substances that bind the analytes are labeled first with ferrimagnetic or ferromagnetic substances and then
(ii) these labeled structure-specific substances are used in a sample that is to be measured,
(iii) the sample that is to be measured is magnetized with a magnetic field that is applied from the outside, and
(iv) after the external field is turned off, the relaxation of the double refraction of the magnetic marker is measured.

The process can also be implemented so that
(i) analytes first are labeled with ferrimagnetic or ferromagnetic substances, and then
(ii) these magnetically labeled analytes are used in a sample that is to be measured, to which substances were added that specifically bind the analytes, and
(iii) the sample that is to be measured is magnetized with a magnetic field that is applied from the outside, and
(iv) after the external field is turned off, the relaxation of the double refraction of the magnetic marker is measured.

The evaluation of the measuring results is carried out here, as also in the competitive assay processes that are described below, in a way that is known to one skilled in the art, i.e., analogously to the processes as they are used in immunoassays or radioassays.

In both previously mentioned cases, the measurement of the double refraction that is changed by the binding can also be used for analysis in the frequency range.

The discrimination between bonded and unbonded markers that are possible to date only in exceptional cases is made possible by the use of their different relaxation mechanisms or the influence of the relaxation time of the magnetic marker that is caused by the binding.

In a liquid phase, analytes can be identified in that the structure-specific substances that bind the analytes first
(i) are labeled with ferrimagnetic or ferromagnetic substances, whereby these substances are selected so that the Brownian relaxation of at least a portion of these substances has a shorter relaxation time under the measuring conditions than the Neelian relaxation and then
(ii) these magnetically labeled substances are used in a sample that is to be measured, and
(iii) the sample that is to be measured is magnetized with a magnetic field of suitable strength that is applied from the outside, and
(iv) after the external field is turned off, the relaxation of the double refraction is measured, whereby the different relaxation behavior of the magnetic markers that are bonded to the analytes compared to the unbonded magnetic markers is used for analysis.

As a measurement variable, the double refraction of the sample can also be determined in the frequency range.

Also in this case, it is possible to combine the analytes that are to be identified, instead of structure-specific substances, with the magnetic labelings.

Structure-specific substances are defined as all substances that bind specifically to certain structures. Structure-specific substances are defined as especially antibodies, antibody fragments, biotin, or substances that bind biotin such as avidin or streptavidin, extravidin or neutravidin, agonists that bind specifically to receptors, such as cytokines, lymphokines, endothelins or their antagonists, specific peptides and proteins, receptors, enzymes, enzyme substrates, nucleotides, ribonucleic acids, deoxyribonucleic acids, carbohydrates, lipoproteins, etc. As structure-specific substances, substances are preferred whose binding constant lies in the range of $10^5$–$10^{15}$ $(mol/l)^{-1}$. Especially preferred are substances whose binding constant is in the range of $10^7$–$10^{15}$ $(mol/l)^{-1}$.

The structure-specific substances or analytes that are to be identified can be labeled with the ferrimagnetic or ferromagnetic particles with the aid of processes that are familiar in immunochemistry, peptide chemistry, and protein chemistry. Especially advantageous are covalent bonds between the structure-specific substances or the analytes that are to be identified with the substances that form the stabilizing shell of ferrimagnetic or ferromagnetic particles. Examples of especially suitable methods are activation and coupling with the aid of carbodiimides [Jakoby and Wilchek, eds.; Methods Enzymol. (1974) 34], the formation of Schiff bases after periodates are exposed to compounds that contain carbohydrates (Wichek and Bayer, eds., Methods Enzym 184:177), which are then optionally reduced for further stabilization, coupling with the aid of glutaric dialdehyde [Heitzmann and Richards, Proc. Natl. Acad. Sci. USA 71 (1974) 3537], cross-linking of bromoacetylated particles with thiolylated substances [Angerer et al.; Cell 9 (1976) 81], as well as reductive alkylation (Bayer et al.: J. Histochem. Cytochem. 24 (1976) 933].

As substances for magnetic labeling, all ferromagnetic or ferrimagnetic materials can be used that can be dispersed in a medium that is suitable for detection, whereby the Neelian relaxation time of at least a part of the magnetic labelings under the measurement conditions is longer than the Brownian relaxation time of these magnetic labelings. Especially suitable are all ferromagnetic or ferrimagnetic colloidal particles with Brownian relaxation times in aqueous media in the range of $10^{-8}$–$10^{-1}$ second and correspondingly longer Neelian relaxation times. To carry out the measurements, the viscosity of the dispersing medium used must be matched to the relaxation times of the ferromagnetic and ferrimagnetic particles and the measurement time since the suspension medium basically determines the time constant of Brownian relaxation. In this case, the temperature dependency of the viscosity of the dispersing medium is taken into consideration.

Preferred are especially ferromagnetic or ferrimagnetic colloidal particles that are made of iron, iron oxides, barium ferrites, strontium ferrites, cobalt, nickel, nickel ferrites, cobalt ferrites, and chromium dioxide, whose Neelian relaxation time is longer than the Brownian relaxation time.

The use of magnetic labelings with narrowly distributed particle sizes and/or magnetic moments or Brownian and Neelian relaxation times is generally advantageous. Separation of magnetic labelings into fractions with a narrow distribution of particle sizes can be achieved by, e.g., chromatographic processes or by using special filtration processes (e.g., glass capillary systems or tangential filtration), by using molecular sieves, or by means of centrifuging. Magnetic labelings with moments that are as uniform as possible can be produced by, e.g., classification in a magnetic gradient field.

The ferromagnetic and ferrimagnetic substances can be stabilized with a shell that is made of oligomeric or polymeric carbohydrates, proteins, peptides, nucleotides, surfactants, other monomers, oligomers, or polymers and/or lipids.

The particle sizes of the ferromagnetic and ferrimagnetic substances are advantageously between 1 nm and 100 nm. Preferred are colloidal particles with particle sizes of between 1 nm and 400 nm. Especially preferred are particle sizes of between 1 nm and 100 nm.

As magnetic markers, ferromagnetic or ferrimagnetic substances can also be produced with a stabilizing shell that is made of the structure-specific substance or the analyte that is to be identified, by the particles being put after production directly into a solution of the structure-specific substance, optionally in the presence of other adjuvants, such as, e.g., proteins, carbohydrates, as well as natural, synthetic, or partially synthetic surface-active substances, etc., or by being produced directly in the presence of structure-specific substances.

Suitable magnetic markers and suspensions that contain these particles are described in, for example, WO 92/12735, WO 92/22586, EP 0 186 616 and U.S. Pat. No. 4,101,435. In principle, magnetic particles can also be used that are usually used as contrast media for nuclear resonance tomography, such as, e.g., Resovist, Lumirem, Feridex, Combidex, Abdoscan and Clariscan.

Compounds, which consist of colloidal suspensions of freely movable ferrimagnetic or ferromagnetic particles and structure-specific substances or analytes that are to be identified, were already described in German Patent DE 195 03 664 C2.

The compounds can also consist of combinations of several ferromagnetic or ferrimagnetic particles with relaxation times that can be discriminated, since measurement results that can be discriminated individually can be achieved through the use of different magnetic labelings with respectively a very narrow distribution of relaxation times and/or magnetic moments for various structure-specific substances or analytes inside a sample. As a result, direct simultaneous determination of several analytes is made possible.

As suspension media, all liquids in which the compounds can move freely are suitable. Especially suitable are water, aqueous solutions of surface-active adjuvants, such as, e.g., surfactants or oligomeric or polymeric carbohydrates and proteins, as well as mixtures of water with alcohols, such as, e.g., glycerol and polyethylene glycol. The suspension media can additionally contain adjuvants that change the osmotic pressure, such as, e.g., common salt. In addition, buffer substances that determine pH, such as, e.g., phosphates, can be contained. Especially preferred are suspension media with suitable optical properties, such as lower absorption and double refraction. As an alternative, the light source can be selected so that as little light as possible is absorbed from the suspension medium, and especially also biological suspension media can be used.

The compounds that consist of ferromagnetic or ferrimagnetic colloidal particles with structure-specific substances or analytes that are to be identified can also be present in dried form, optionally in combination with other adjuvants which, e.g., facilitate drying or increase the stability of the dried product (e.g., as lyophilizates) and are converted into the suspension medium only shortly before the measurement.

Due to the binding identification based on physical mechanisms, non-specific measurement signals (matrix phenomena) can be largely ruled out. The specificity of the process thus depends only on the "true" specificity of the structure-specific substance (cross reactivity of antibodies, non-specific binding of ligands). Based on the high sensitivity of the process according to the invention, it is easy to remain under the other commonly used detection limits of binding assays.

The process according to the invention can be used in, e.g., fertility, histocompatibility, allergology, infectiology, hygiene, genetics, virology, bacteriology, toxicology, pathology, environmental analysis, food chemistry and medical diagnosis.

The following examples are used for a more detailed explanation of the subject of the invention, without intending that they be limited to this subject.

EXAMPLES

1. Measurement of a Series of Dilutions of Dextran-Magnetite:

Procedure:

The starting sample (iron oxide that is coated with dextran, produced according to the method of M. Hasegawa and S. Hakukoku, U.S. Pat. No. 4,101,435 (1978), manufacturer: Meito Sangyo) was present at a concentration of 1 mol of Fe/l. From this, in each case, samples diluted with distilled water by the factor 10 were produced (concentration range of $10^{-1}$ to $10^{-6}$ mol of Fe/l). A comparison sample with distilled water was also examined. For measurement, a volume of 1 ml of all samples was loaded into the optical cell.

All measurements produced here were performed with the same procedure. The samples were magnetized for a period of 2 ms repeatedly with a magnetic pulse of strength 100 Oe (10 mT). The pause between the pulses was 20 ms. To improve the signal-noise ratio, 256 individual measurements were averaged.

Figure 2:
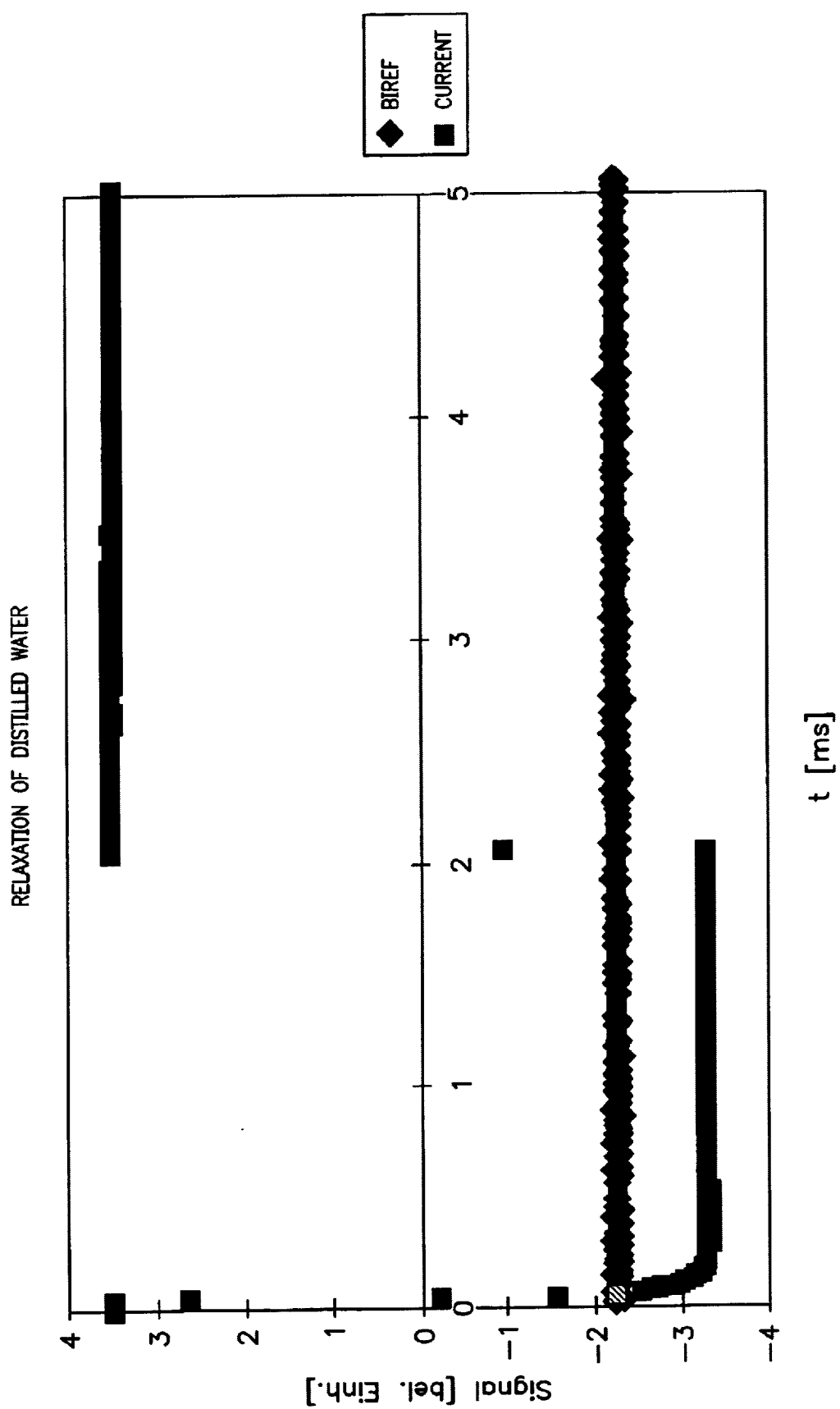
Figure 3:
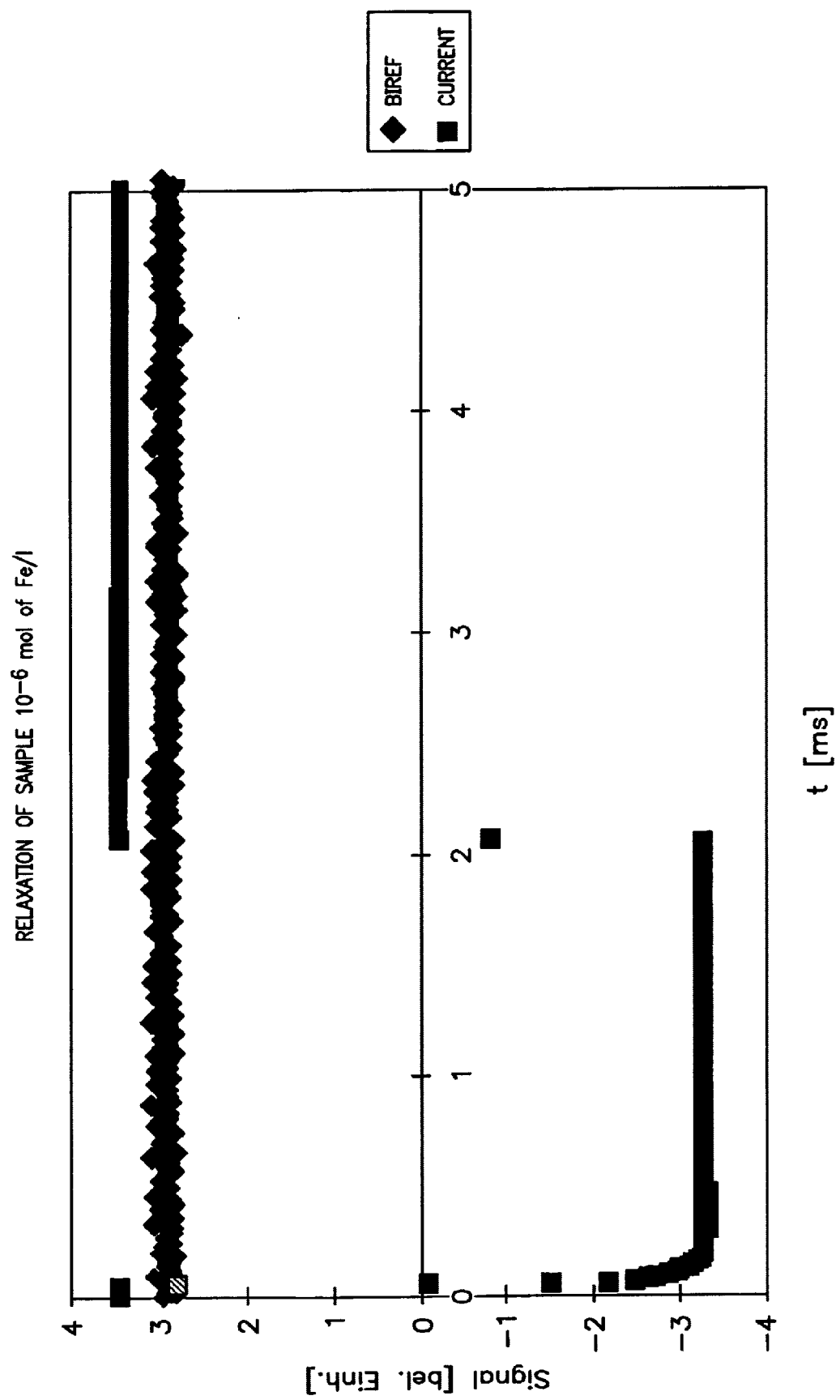

Result:

For the comparison sample with distilled water and the sample of concentration of $10^{-6}$ mol of Fe, no relaxation signal could be detected (cf. FIG. 2 or FIG. 3).

Figure 4:
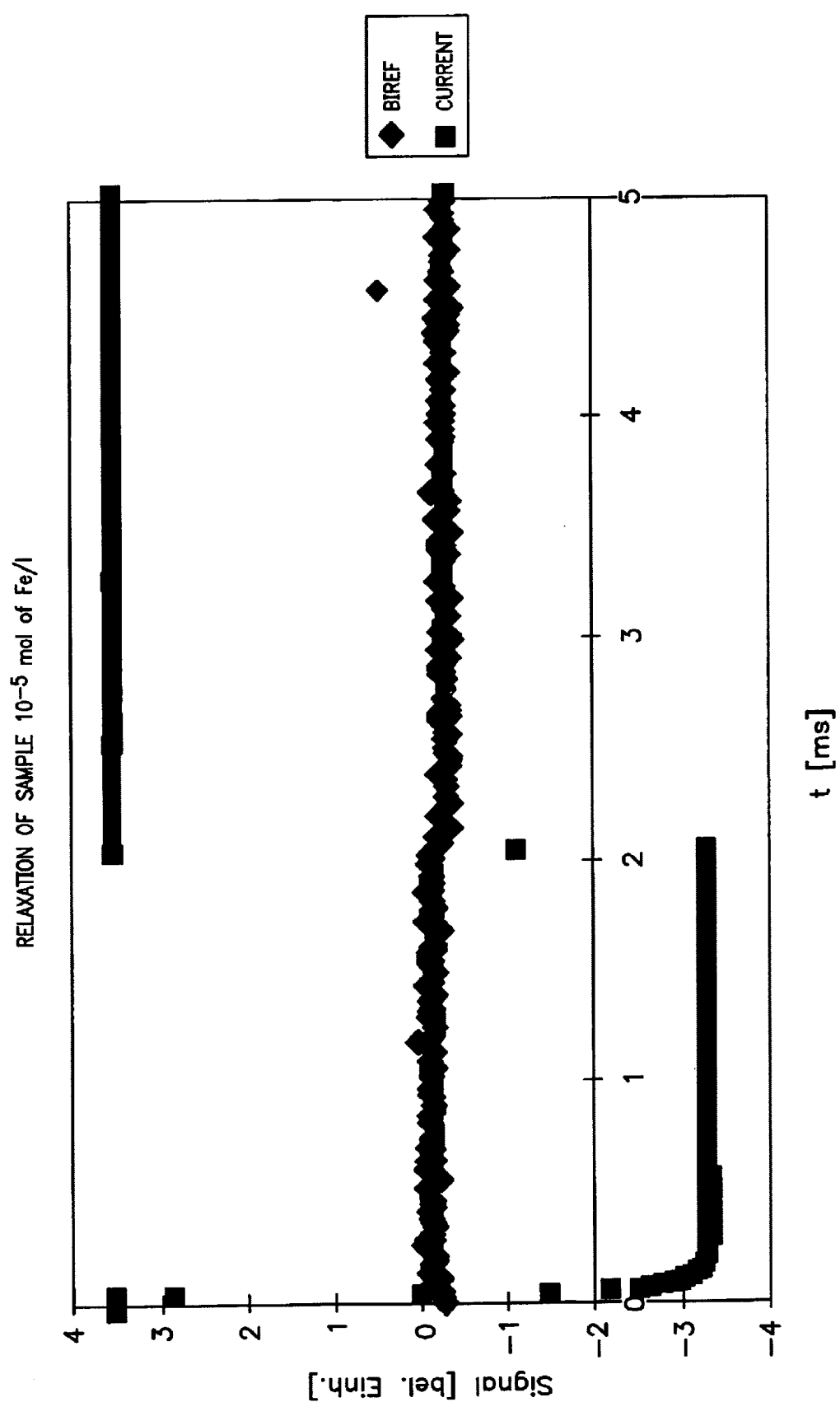

The relaaxation of a sample of the concentration of $10^{-5}$ mol/l of Fe was detectable and is shown in FIG. 4.

The amount of Fe substance contained in the sample volume of 1 ml of this sample is 10 nmol. It is observed that actually only the volume of about 2×2×10 mm (40 $\mu$l) that is in the laster beam contributes to the signal, and a detection amount of 0.4 nmol of Fe is produced. This is on the order of the detection sensitivity of the process that is described in DE 195 03 664 C2. The new measuring position was not specially optimized to a high detection sensitivity. The particles that are used contain only a very small fraction of particles that are lined up according to Brown and thus contribute to the signal.

2. Measurement of the Influence of the Addition of Biotin-BSA to Dextran-Magnetite that is Coupled with Streptavidin in the Relaxation of the Double Refraction Procedure:

The sample (dextran-magnetite of Example 1, coupled with streptavidin) was present in an initial concentration of 2.66 mmol of Fe/l. For the measurements, a sample 1 that consists of 100 $\mu$l of the sample that is diluted with 400 $\mu$l of BSA-PBS (PBS: phosphate buffered saline) buffer was produced. The relaxation signal of this sample was measured. Then, 40 $\mu$l of biotin-BSA that was diluted in BSA-PBS buffer (absolute amount of 400 ng of biotin-BSA) was added one time to this sample. Then, the relaxation signal was measured at various times after mixing.

As a control, a sample 2 that consists of 100 $\mu$l of dextran-magnetite, coupled with streptavidin (diluted in 400$\mu$l of BSA-PBS buffer), was saturated with 5 $\mu$l of free biotin (1:10 diluted, initial concentration of 1 mg/ml). Also, here, 40 $\mu$l of biotin-BSA diluted in BSA-PBS buffer (absolute amount 400 ng of biotin-BSA) was added one time, and the relaxation signal was measured at various times after mixing.

Result:

The relaxation signal of sample 1 was clearly observable. After biotin-BSA was added, a significant increase in the relaxation time was shown. This extension of the relaxation time can be explained by the increase of the hydrodynamic particle diameter of the sample by biotin-BSA-induced aggregation or cross-linking.

Sample 2 also showed a clear relaxation signal. The addition of biotin-BSA in the BSA-PBS buffer to this sample did not result, however, in a change of the relaxation time.

The unchanged hydrodynamic particle diameter that is to be concluded from the above shows that by the saturation of the binding sites of streptavidin with free biotin, it no longer results in an aggregation or cross-linking of the sample that is induced by biotin-BSA. Thus, the specificity of the binding reaction was demonstrated in sample 1.

What is claimed is:

1. A process for detecting an analyte or a binding reaction, in a binding assay conducted in a sample labeled with a ferromagnetic or ferrimagnetic substance comprising determining double refraction behavior or relaxation behavior of double refraction in the sample, and correlating said behavior with the presence of the analyte or binding reaction.

2. A process for detecting an analyte or a binding reaction according to claim 1, wherein Brownian relaxation in at least a part of the ferromagnetic or ferrimagnetic substance proceeds faster than Néelian relaxation.

3. A process according to claim 1, wherein the structure-specific substances are antibodies, antibody fragments, biotin, or substances that specifically bind biotin.

4. A process according to claim 3, wherein the structure-specific substances have a binding constant in the range of $10^5$–$10^{15}$ $(mol/l)^{-1}$.

5. A process according to claim 3, wherein the structure-specific substances are avidin, streptavidin, neutravidin, or extravidin.

6. A process according to claim 3, wherein the structure-specific substances are agonists that bind specifically to receptors or their antagonists, peptides, proteins, receptors, enzymes, enzyme substrates, nucleotides, ribonucleic acids, deoxyribonucleic acids, carbohydrates, or lipoproteins.

7. A process according to claim 6, wherein the agonists that bind to receptors are cytokines, lymphokines, or endothelins.

8. A process according to claim 1, wherein the ferromagnetic or ferrimagnetic substances have a particle size in the range of 1 nm to 100 $\mu$m.

9. A process according to claim 1, wherein the ferromagnetic or ferrimagnetic substance is stabilized with a shell that comprises oligomeric or polymeric carbohydrates, proteins, peptides, nucleotides and/or lipids.

10. A process according to claim 1, wherein said analyte or binding reaction is one involved in fertility, histocompatibility, allergology, infectiology, hygiene, genetics, virology, bacteriology, toxicology, pathology, environmental analysis, food chemistry or medical diagnosis comprising a process for detecting analytes or binding reactions according to claim 1.

11. A process according to claim 1, wherein detecting is accomplished by an apparatus that contains a light polarizer, a device that receives a sample, a device that magnetizes the sample with magnetic pulses or a magnetic field of variable frequency, and an analyzer that analyzes the polarization direction of polarized light.

12. A process according to claim 9, wherein the apparatus contains an optical bank, a laser, a polarizer, an optical cell containing the sample, an analyzer and a photodetector.

13. A process according to claim 11, wherein the apparatus further comprises a $\lambda$/4-plate between the sample and the analyzer.

14. A process according to claim 1, wherein determining double refraction behavior comprises exposing the sample to an alternating magnetic field and measuring the double refraction as a function of distance and phase relative to the magnetizing field.

15. A process for detecting an analyte or a binding reaction, in a binding assay, comprising labeling a sample with a ferromagnetic or ferrimagnetic substance and determining the double refraction behavior or relaxation behavior of double refraction in the sample and correlating said behavior with the presence of the analyte or binding reaction.

16. A process according to claim 15, wherein Brownian relaxation in at least a part of the ferromagnetic or ferrimagnetic substances proceeds faster than Néelian relaxation.

17. A process according to claim 15, wherein determining double refraction behavior comprises exposing the sample to an alternating magnetic field and measuring the double refraction as a function of distance and phase relative to the magnetizing field.

18. A process for detecting an analyte or a binding reaction in a sample, comprising
   (i) adding to the sample a structure-specific substance that binds an analyte labeled with a ferrimagnetic or ferromagnetic substance, or adding to the sample a structure-specific substance labeled with a ferromagnetic or ferromagnetic substance that binds an analyte,
   (ii) magnetizing the sample with a magnetic field, and
   (iii) after the magnetic field is turned off or removed, measuring the double refraction behavior or relaxation behavior of double refraction in the sample, and correlating said behavior with the presence of the analyte or binding reaction.

19. A process according to claim 18, wherein the magnetic field is applied from an external source.

20. A process according to claim 18, wherein a structure-specific substance that binds an analyte labeled with a ferrimagnetic or ferromagnetic substance is added to the sample.

21. A process according to claim 18, wherein a structure-specific substance labeled with a ferromagnetic or ferromagnetic substance that binds an analyte is added to the sample.

22. A process according to claim 18, wherein determining double refraction behavior comprises exposing the sample to an alternating magnetic field and measuring the double refraction as a function of distance and phase relative to the magnetizing field.

23. A process according to claim 18, wherein the structure-specific substance or analyte is immobilized.

24. A process for detecting an analyte or a binding reaction, comprising
   (i) labeling an analyte or a structure-specific substance with a ferrimagnetic or ferromagnetic substance,
   (ii) magnetizing a sample containing the resultant labeled analyte and a substance that specifically binds the analyte or a sample containing the resultant labeled structure-specific substance and analyte that specifically binds the substance with a magnetic field, and
   (iii) after the magnetic field is turned off or removed, measuring the double refraction behavior or relaxation behavior of double refraction in the sample, and correlating said behavior with the presence of the analyte or binding reaction.

25. A process according to claim 24, wherein the magnetic field is applied from an external source.

26. A process according to claim 24, wherein an analyte is labeled with a ferrimagnetic or ferromagnetic substance.

27. A process according to claim 24, wherein a structure-specific substance is labeled with a ferrimagnetic or ferromagnetic substance.

28. A process according to claim 24, wherein determining double refraction behavior comprises exposing the sample to an alternating magnetic field and measuring the double refraction as a function of distance and phase relative to the magnetizing field.

29. A process for detecting an analyte in a liquid phase, comprising
   (i) labeling a structure-specific substance that binds the analyte or labeling an analyte that binds a structure-specific substance with a ferrimagnetic or ferromagnetic substance, wherein Brownian relaxation in at least a part of the ferromagnetic or ferromagnetic substance has a shorter relaxation time than Néelian relaxation,
   (ii) magnetizing the liquid phase that contains the resultant labeled analyte or resultant labeled substance with a magnetic field,
   (iii) after the magnetic field is turned off or removed, measuring the double refraction behavior or relaxation behavior of the double refraction in the liquid phase, and
   (iv) comparing the varying double refraction behavior or relaxation behavior of double refraction of the labeled substances that are bonded to the analytes or of the labeled analytes that are bonded to the substances with the double refraction behavior or relaxation behavior of double refraction of the labeled substances that are not bound to analytes or with the double refraction behavior or relaxation behavior of double refraction of the labeled analytes that are not bound to labeled substances, and correlating said behavior with the presence of the analyte or binding reaction.

30. A process according to claim 29, wherein the magnetic field is applied from an external source.

31. A process according to claim 29, wherein an analyte is labeled with a ferrimagnetic or ferromagnetic substance.

32. A process according to claim 29, wherein a structure-specific substance is labeled with a ferrimagnetic or ferromagnetic substance.

33. A process for detecting two or more different analytes or two or more different binding reactions in a sample comprising
   (i) adding to the sample two or more different structure-specific substances that bind two or more different analytes, each independently, labeled with a ferrimagnetic or ferromagnetic substance, wherein the ferrimagnetic or ferromagnetic substance in each case is different, or adding to the sample two or more different structure-specific substances, each independently, labeled with a ferrimagnetic or ferromagetic substance, wherein the ferrimagnetic or ferromagnetic substance in each case is different, and wherein said two or more different structure-specific substances bind two or more different analytes,
   (ii) magnetizing the sample with a magnetic field, and
   (iii) after the magnetic field is turned off or removed, measuring the double refraction behavior or relaxation behavior of double refraction in the sample, and correlating said behavior with the presence of the two or more analytes or two or more binding reactions.

34. A process according to claim 33, wherein the two or more ferromagnetic or ferrimagnetic substances have Brownian relaxation times that are used are distinguishable from each other.

35. A process according to claim 33, wherein the two or more different structure-specific substances labeled with ferromagnetic or ferromagnetic substances are added to the sample.

36. A process according to claim 33, wherein the two or more different analytes labeled with ferromagnetic or ferromagnetic substances are added to the sample.

37. A process according to claim 33, wherein two more different structure-specific substance or analytes is immobilized.

38. A process for detecting two or more different analytes or two or more different binding reactions in a sample comprising
  (i) labeling two or more different structure-specific substances that bind two or more different analytes, each independently, with a ferrimagnetic or ferromagnetic substance, wherein the ferrimagnetic or ferromagnetic substance in each case is different, or labeling two or more different structure-specific substances, each independently, with a ferrimagnetic or ferromagnetic substance, wherein the ferrimagnetic or ferromagnetic substance in each case is different, and wherein said two or more different structure-specific substances bind two or more different analytes,
  (ii) magnetizing a sample containing the resultant labeled analytes and two or more substances that specifically bind the analytes or a sample containing the resultant labeled structure-specific substances and two or more analytes that specifically bind the substances with a magnetic field, and
  (iii) after the magnetic field is turned off or removed, measuring the double refraction behavior or relaxation behavior of double refraction in the sample, and correlating said behavior with the presence of the analyte or binding reaction.

39. A process according to claim 38, wherein the two or more different structure-specific substances labeled with ferromagnetic or ferromagnetic substances are added to the sample.

40. A process according to claim 38, wherein the two or more different analytes labeled with ferromagnetic or ferromagnetic substances are added to the sample.

41. A process according to claim 38, wherein the sample is in the liquid phase.

* * * * *